United States Patent
Lin (10) Patent No.: US 8,078,272 B2
(45) Date of Patent: *Dec. 13, 2011

(54) SYSTEMS AND METHODS FOR DETECTING OR VALIDATING SIGNALS IN THE PRESENCE OF NOISE

(75) Inventor: Yayun Lin, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1022 days.

This patent is subject to a terminal disclaimer.

(21) Appl. No.: 11/625,432

(22) Filed: Jan. 22, 2007

(65) Prior Publication Data

US 2007/0135722 A1   Jun. 14, 2007

Related U.S. Application Data

(63) Continuation-in-part of application No. 10/213,364, filed on Aug. 6, 2002, now Pat. No. 7,215,993.

(51) Int. Cl.
*A61B 5/0402* (2006.01)
(52) U.S. Cl. ....................................................... 600/518
(58) Field of Classification Search .......... 600/515–518, 600/521
See application file for complete search history.

(56) References Cited

U.S. PATENT DOCUMENTS

| | | | |
|---|---|---|---|
| 4,432,362 A | 2/1984 | Leckrone et al. | |
| 4,589,420 A | 5/1986 | Adams et al. | |
| 4,679,144 A | 7/1987 | Cox et al. | |
| 4,779,617 A | 10/1988 | Whigham | |
| 4,913,146 A | 4/1990 | DeCote, Jr. | |
| 4,960,123 A | 10/1990 | Maker | |
| 5,010,887 A | 4/1991 | Thornander | |
| 5,188,117 A | 2/1993 | Steinhaus et al. | |
| 5,209,237 A | 5/1993 | Rosenthal | |
| 5,370,124 A | 12/1994 | Dissing et al. | |
| 5,492,128 A | 2/1996 | Wickham | |
| 5,522,857 A | 6/1996 | van Krieken | |

(Continued)

FOREIGN PATENT DOCUMENTS

JP   2002518110   6/2002

(Continued)

OTHER PUBLICATIONS

Gunderson, Bruce, "Automatic Identification of ICD Lead Problems Using Electrograms", *PACE*, vol. 24, p. 664, Apr. 2002, (2002),664.

(Continued)

*Primary Examiner* — Eric D. Bertram
(74) *Attorney, Agent, or Firm* — Schwegman, Lundberg & Woessner, P.A.

(57) ABSTRACT

Detecting or validating signals such as cardiac beats can be performed in the presence of myopotential or other noise. An amplitude peak, which can be a candidate for a detected beat, can be used in a normalized or other weighted average, along with a preceding and subsequent sample. The weighted average is compared to a noise threshold. Based on the result, the amplitude peak is either deemed an actual beat (e.g., depolarization or repolarization), or noise. The described systems, devices, and methods can improve the accuracy of detecting an actual beat in the presence of noise, during normal sinus rhythm or during an arrhythmia such as ventricular fibrillation. This, in turn, improves the accuracy with which therapy is delivered or withheld by an implantable device.

28 Claims, 7 Drawing Sheets

U.S. PATENT DOCUMENTS

| | | | |
|---|---|---|---|
| 5,562,713 A | 10/1996 | Silvian | |
| 5,564,430 A | 10/1996 | Jacobson et al. | |
| 5,573,550 A | 11/1996 | Zadeh et al. | |
| 5,591,214 A | 1/1997 | Lu | |
| 5,613,495 A * | 3/1997 | Mills et al. | 600/509 |
| 5,647,379 A | 7/1997 | Meltzer | |
| 5,697,958 A | 12/1997 | Paul et al. | |
| 5,702,425 A | 12/1997 | Wickham | |
| 5,702,427 A | 12/1997 | Ecker et al. | |
| 5,709,215 A | 1/1998 | Perttu et al. | |
| 5,755,738 A | 5/1998 | Kim et al. | |
| 5,766,227 A | 6/1998 | Nappholz et al. | |
| 5,778,881 A | 7/1998 | Sun et al. | |
| 5,782,876 A | 7/1998 | Flammang | |
| 5,792,212 A | 8/1998 | Weijand | |
| 5,817,130 A | 10/1998 | Cox et al. | |
| 5,817,135 A | 10/1998 | Cooper et al. | |
| 5,861,008 A | 1/1999 | Obel et al. | |
| 5,865,749 A | 2/1999 | Doten et al. | |
| 5,867,361 A | 2/1999 | Wolf et al. | |
| 5,870,272 A | 2/1999 | Seifried et al. | |
| 5,871,509 A | 2/1999 | Noren | |
| 5,891,171 A | 4/1999 | Wickham | |
| 5,897,575 A | 4/1999 | Wickham | |
| 5,957,857 A | 9/1999 | Hartley | |
| 5,978,710 A | 11/1999 | Prutchi et al. | |
| 5,999,848 A | 12/1999 | Gord et al. | |
| 6,029,086 A | 2/2000 | Kim et al. | |
| 6,031,710 A | 2/2000 | Wolf et al. | |
| 6,063,034 A | 5/2000 | Doten et al. | |
| 6,068,589 A | 5/2000 | Neukermans | |
| 6,070,097 A | 5/2000 | Kreger et al. | |
| 6,097,983 A | 8/2000 | Strandberg | |
| 6,112,119 A | 8/2000 | Schuelke et al. | |
| 6,195,585 B1 | 2/2001 | Karunasiri et al. | |
| 6,198,968 B1 | 3/2001 | Prutchi et al. | |
| 6,201,993 B1 | 3/2001 | Kruse et al. | |
| 6,208,900 B1 | 3/2001 | Ecker et al. | |
| 6,223,083 B1 | 4/2001 | Rosar | |
| 6,230,059 B1 | 5/2001 | Duffin | |
| 6,236,882 B1 | 5/2001 | Lee et al. | |
| 6,272,381 B1 | 8/2001 | Callaghan et al. | |
| 6,282,446 B1 | 8/2001 | Eberle et al. | |
| 6,321,115 B1 | 11/2001 | Mouchawar et al. | |
| 6,421,554 B1 | 7/2002 | Lee et al. | |
| 6,505,071 B1 | 1/2003 | Zhu et al. | |
| 6,892,092 B2 | 5/2005 | Palreddy et al. | |
| 6,917,830 B2 * | 7/2005 | Palreddy et al. | 600/509 |
| 7,215,993 B2 * | 5/2007 | Lin | 600/521 |
| 7,467,009 B2 | 12/2008 | Palreddy et al. | |
| 2003/0083713 A1 | 5/2003 | Palreddy et al. | |
| 2004/0106957 A1 | 6/2004 | Palreddy et al. | |
| 2005/0192504 A1 | 9/2005 | Palreddy et al. | |
| 2009/0093731 A1 | 4/2009 | Palreddy et al. | |

FOREIGN PATENT DOCUMENTS

| | | |
|---|---|---|
| WO | WO-9965565 | 12/1999 |
| WO | WO-01/43820 | 6/2001 |
| WO | WO-2005018738 A1 | 3/2005 |
| WO | WO-2005018738 A1 | 3/2005 |

OTHER PUBLICATIONS

Morris, W., "American Heritage Dictionary—2nd Edition", *Boston : Houghton Mifflin*, Property of U.S.Government,(1982),74, 269, and 283.

"European Application Serial No. 03767175.7, Office Action mailed Mar. 11, 2010", 5 pgs.

"Japanese Application Serial No. 2006-524060, Office Action mailed Apr. 16, 2010", 5 pgs.

"European Application No. 03767175.7; Response filed Sep. 21, 2010 to Office Action mailed Mar. 11, 2010", 13 pgs.

"File Wrapper History of U.S. Appl. No. 10/046,650", 34 pgs, 2009.

"File Wrapper History of U.S. Appl. No. 11/110,490", 24 pgs, 2009.

"Japanese Application Serial No. 2006-524060, Office Action mailed Oct. 22, 2010", 2 pgs.

"Japanese Application Serial No. 2006-524060, Response filed Jan. 21, 2011 to Non-Final Office Action mailed Oct. 22, 2010", 7 pgs.

"U.S. Appl. No. 10/046,650, Non Final Office Action mailed Jun. 24, 2004", 9 pgs.

"U.S. Appl. No. 10/046,650, Response filed Sep. 28, 2004 to Non Final Office Action mailed Jun. 24, 2004", 12 pgs.

"U.S. Appl. No. 10/213,364, Advisory Action mailed Jan. 9, 2006", 3 pgs.

"U.S. Appl. No. 10/213,364, Examiner Interview Summary mailed Jul. 27, 2006", 2 pgs.

"U.S. Appl. No. 10/213,364, Final Office Action mailed May 12, 2006", 10 pgs.

"U.S. Appl. No. 10/213,364, Final Office Action mailed Jul. 27, 2006", 12 pgs.

"U.S. Appl. No. 10/213,364, Final Office Action mailed Oct. 14, 2005", 9 pgs.

"U.S. Appl. No. 10/213,364, Non Final Office Action mailed Feb. 7, 2006", 8 pgs.

"U.S. Appl. No. 10/213,364, Non Final Office Action mailed May 25, 2005", 7 pgs.

"U.S. Appl. No. 10/213,364, Notice of Allowance mailed Oct. 4, 2006", 7 pgs.

"U.S. Appl. No. 10/213,364, Response filed Jan. 13, 2006 to Advisory Action mailed Jan. 9, 2006", 12 pgs.

"U.S. Appl. No. 10/213,364, Response filed May 8, 2006 to Non Final Office Action mailed Feb. 7, 2006", 12 pgs.

"U.S. Appl. No. 10/213,364, Response filed Jul. 12, 2006 to Final Office Action mailed May 12, 2006", 12 pgs.

"U.S. Appl. No. 10/213,364, Response filed Sep. 20, 2005 to Non Final Office Action mailed May 25, 2005", 10 pgs.

"U.S. Appl. No. 10/213,364, Response filed Sep. 27, 2006 to Final Office Action mailed Jul. 27, 2006", 11 pgs.

"U.S. Appl. No. 10/213,364, Response filed Dec. 12, 2005 to Final Office Action mailed Oct. 14, 2005", 11 pgs.

"U.S. Appl. No. 10/643,770, Non Final Office Action mailed Jun. 24, 2004", 7 pgs.

"U.S. Appl. No. 10/643,770, Response filed Oct. 25, 2004 to Non Final Office Action mailed Jun. 24, 2004", 11 pgs.

"U.S. Appl. No. 11/110,490, Non Final Office Action mailed Mar. 14, 2008", 8 pgs.

"U.S. Appl. No. 11/110,490, Response filed Jun. 3, 2008 to Non Final Office Action mailed Mar. 14, 2008", 12 pgs.

\* cited by examiner

SYSTEMS AND METHODS FOR DETECTING OR VALIDATING SIGNALS IN THE PRESENCE OF NOISE

CROSS REFERENCE TO RELATED APPLICATIONS

This patent application is a continuation-in-part of Yayun Lin U.S. patent application Ser. No. 10/213,364, now issued as U.S. Pat. No. 7,215,993, entitled CARDIAC RHYTHM MANAGEMENT SYSTEMS AND METHODS FOR DETECTING OR VALIDATING CARDIAC BEATS IN THE PRESENCE OF NOISE, which was filed on Aug. 6, 2002, and which is incorporated by reference herein in its entirety.

TECHNICAL FIELD

This document relates generally to medical systems, devices, and methods, and particularly, but not by way of limitation, to systems and methods for detecting and/or validating signals, even in the presence of noise.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and repolarizations and those associated with ventricular depolarizations ("QRS complexes") or repolarizations.

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem faced by cardiac rhythm management devices is in detecting the atrial and/or ventricular depolarizations or repolarizations in the intrinsic electrical cardiac signals, since the delivery of therapy to the heart is typically based at least in part on the timing and/or morphology of such detected depolarizations or repolarizations. To detect a depolarization or repolarization event, the cardiac signal may be amplified, filtered, and/or level-detected (e.g., to determine whether an artifact exceeds a particular threshold level associated with an atrial or ventricular depolarization or repolarization). Depolarization or repolarization detection is complicated, however, by the fact that the intrinsic cardiac signals may include noise unrelated to the heart depolarization or repolarization. The noise may arise from a variety of sources, including, among other things: myopotentials associated with skeletal muscle contractions; a loose or fractured leadwire providing intermittent contact between the device and the heart; or, electromagnetic interference from AC power provided to nearby electrical equipment (e.g., 60 Hertz), from nearby switching power supplies, from a nearby electrosurgical tool, from communication equipment, or from electronic surveillance equipment. Noise erroneously detected as a heart depolarization or repolarization may inappropriately inhibit bradyarrhythmia pacing therapy or cardiac resynchronization therapy, or may inappropriately trigger tachyarrhythmia shock therapy. For these and other reasons, the present inventor has recognized a need for improved techniques for discriminating between a depolarization or repolarization, which is associated with a cardiac beat, and noise, which is not.

SUMMARY

This document discusses, among other things, systems devices and methods for detecting or validating signals, such as depolarizations or repolarizations, in the presence of noise.

Example 1 includes a system comprising a cardiac or other physiologic signal detector and a signal processor circuit. In this example, the signal detector comprises a detector input configured to be coupled to a first electrode associated with a heart. A detector output provides a sampled signal. A signal processor circuit is coupled to the detector output. The signal processor circuit is configured to distinguish, using a peak sample, a preceding sample to the peak sample, and a subsequent sample to the peak sample, a depolarization or repolarization from noise. The signal processor circuit is configured to form an central tendency statistic (such as an average, mean, median, mode, weighted average, normalized weighted average, etc.) computed using as data points an amplitude of the peak sample from a baseline, an amplitude of the preceding sample from the same baseline, and an amplitude of the subsequent sample from the same baseline. The signal processor circuit is configured to distinguish a depolarization or repolarization from noise by comparing the statistic to a specified threshold value.

In Example 2, the system of Example 1 optionally configures the signal processor circuit to compute a weighted average using the peak sample, the preceding sample, and the subsequent sample. In this example, the signal processor circuit distinguishes a depolarization or repolarization from noise by comparing the weighted average to a specified threshold value.

In Example 3, the system of one or more of Examples 1 or 2 is optionally configured to compute a normalized weighted average using the peak sample, the preceding sample, and the subsequent sample, and to distinguish a depolarization or repolarization from noise by comparing the normalized weighted average to a specified threshold value.

In Example 4, the system of one or more of Examples 1-3 is optionally configured using a normalized weighted average that is computed as $NWA=[P(n-1)+2*P(n)+P(n+1)]/[4*P(n)]$.

In Example 5, the system of one or more of Examples 1-4 optionally further comprises an electrode coupled to the detector input.

In Example 6, the system of one or more of Examples 1-5 optionally further comprises an intracardiac leadwire carrying the electrode.

In Example 7, the system of one or more of Examples 1-6 optionally further comprises an implantable device including the signal detector and the signal processing circuit, and a remote user interface, configured to be communicatively coupled to the implantable device.

In Example 8, the system of one or more of Examples 1-7 comprises the signal processor circuit configured to distinguish a normal sinus rhythm depolarization or repolarization from noise.

In Example 9, the system of one or more of Examples 1-8 comprises the signal processor circuit configured to distinguish an arrhythmic depolarization or repolarization from noise.

In Example 10, the system of one or more of Examples 1-9 comprises the signal processor circuit configured to distinguish a ventricular fibrillation from noise.

In Example 11, a device comprises a signal detector, a depolarization or repolarization detector circuit, and a signal processor circuit. In this example, the signal detector comprises a signal detector input configured to be coupled to a first electrode associated with a heart to receive an intrinsic signal therefrom. The signal detector also comprises a signal detector output providing a sampled signal. A depolarization or repolarization detector circuit is coupled to the first electrode. The depolarization or repolarization detector circuit includes a level detector circuit configured to detect an intrinsic heart depolarization on the intrinsic cardiac signal. A signal processor circuit is coupled to the signal detector output and the depolarization or repolarization detector circuit. The signal processor circuit is configured to validate the intrinsic heart depolarization or repolarization detected by the depolarization or repolarization detector circuit by distinguishing a depolarization or repolarization from noise, such as by using a central tendency statistic computed using as data points an amplitude, from a baseline, of a peak sample of the sampled signal, an amplitude, from the same baseline, of a preceding sample to the peak sample of the sampled signal, and an amplitude, from the same baseline, of a subsequent sample to the peak sample of the sampled signal, wherein the peak sample of the sampled signal is associated with a peak of the intrinsic heart depolarization or repolarization detected by the depolarization detector circuit.

In Example 12, the device of Example 11 optionally comprises the signal processor circuit being configured to compute a weighted average using the peak sample, the preceding sample, and the subsequent sample, and to distinguish a depolarization or repolarization from noise by comparing the weighted average to a specified threshold value.

In Example 13, the device of one or more of Examples 11-12 optionally comprises the weighted average is computed as $NWA=[P(n-1)+2*P(n)+P(n+1)]/[4*P(n)]$.

In Example 14, the device of one or more of Examples 11-13 optionally comprises the signal processor circuit is configured to distinguish a normal sinus rhythm depolarization or repolarization from noise.

In Example 15, the device of one or more of Examples 11-14 optionally comprises the signal processor circuit being configured to distinguish an arrhythmic depolarization or repolarization from noise.

In Example 16, the device of one or more of Examples 11-15 optionally comprises the signal processor circuit is configured to distinguish a ventricular fibrillation from noise.

In Example 17, a method comprises: sampling a cardiac or other physiologic signal; detecting a peak sample from the cardiac signal; detecting a preceding sample to the peak sample from the signal; detecting a subsequent sample to the peak sample from the signal; distinguishing, using the peak sample, the preceding sample, and the subsequent sample, a depolarization or repolarization from noise. The distinguishing the depolarization or repolarization from noise comprises: computing a central tendency statistic, the statistic computed using as data points an amplitude of the peak sample from a baseline, an amplitude of the preceding sample from the same baseline, and an amplitude of the subsequent sample from the same baseline; and distinguishing a depolarization or repolarization from noise by comparing the statistic to a specified threshold value.

In Example 18, the method of Example 17 optionally is performed such that the computing comprises computing a weighted average using the peak sample, the preceding sample, and the subsequent sample, and distinguishing a depolarization or repolarization from noise by comparing the weighted average to a specified threshold value.

In Example 19, the method of one or more of Examples 17-18 optionally is performed such that the computing comprises computing a normalized weighted average using the peak sample, the preceding sample, and the subsequent sample, and distinguishing a depolarization or repolarization from noise by comparing the normalized weighted average to a specified threshold value.

In Example 20, the method of one of more of Examples 17-19 optionally is performed such that the computing the normalized weighted average is computed as $NWA=[P(n-1)+2*P(n)+P(n+1)]/[4*P(n)]$.

In Example 21, the method of one or more of Examples 17-20 optionally comprises communicating an indication of whether a peak sample is a depolarization or repolarization or noise to a remote location.

In Example 22, the method of one or more of Examples 17-21 is optionally performed such that the distinguishing a depolarization or repolarization from noise comprises distinguishing a normal sinus rhythm depolarization or repolarization from noise.

In Example 23, the method of one or more of Examples 17-22 is optionally performed such that the distinguishing a depolarization or repolarization from noise comprises distinguishing an arrhythmic depolarization or repolarization from noise.

In Example 24, the method of one or more of Examples 17-23 is optionally performed such that the distinguishing a depolarization or repolarization from noise comprises distinguishing a ventricular fibrillation from noise.

In Example 25, a method comprises: detecting an intrinsic cardiac or other physiologic signal; detecting a depolarization or repolarization on the intrinsic signal by comparing a level of the intrinsic signal to a level threshold value to yield a level-detected depolarization or repolarization; sampling the intrinsic signal to produce a sampled signal; detecting a peak sample from the sampled signal, wherein the peak sample is associated with the level-detected depolarization or repolarization; detecting a preceding sample to the peak sample from the sampled signal; detecting a subsequent sample to the peak sample from the sampled signal; and validating, using the peak sample, the preceding sample, and the subsequent sample, the level-detected depolarization or repolarization by computing a weighted average using the peak sample, the preceding sample, and the subsequent sample, and comparing the weighted average to a noise threshold.

In Example 26, the method of Example 25 is optionally performed such that the computing the weighted average is computed as $NWA=[P(n-1)+2*P(n)+P(n+1)]/[4*P(n)]$.

In Example 27, the method of one or more of Examples 25-26 is optionally performed such that the validating comprises validating a normal sinus rhythm depolarization or repolarization.

In Example 28, the method of one or more of Examples 25-27 is optionally performed such that the validating comprises validating an arrhythmic depolarization or repolarization from noise.

In Example 29, the method of one or more of Examples 25-28 is optionally performed such that the validating comprises validating a ventricular fibrillation from noise.

In Example 30, a system comprises a cardiac or other physiologic signal detector and a signal processor circuit. The signal detector comprises a detector input configured to be coupled to a first electrode associated with a heart. The signal detector also comprises a detector output providing a sampled signal. The signal processor circuit is coupled to the detector output. The signal processor circuit is configured to distinguish a depolarization or repolarization from noise. The distinguishing the depolarization or repolarization from noise uses an amplitude of a peak sample from a baseline, an amplitude, from the same baseline, of a preceding sample to the peak sample, and an amplitude, from the same baseline, of a subsequent sample to the peak sample. The signal processor circuit is configured to form an average of each of the amplitudes of the peak sample, the preceding sample, and the subsequent sample, and to distinguish a depolarization or repolarization from noise by comparing the average to a specified threshold value.

This document also includes data that illustrates the detecting/validating during normal sinus rhythm, as well as during an arrhythmia, such as the onset of ventricular fibrillation. Other aspects of the present systems, devices, and methods will become apparent upon reading the following detailed description and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s)

should be considered supplementary to that of this document; for irreconcilable inconsistencies, the usage in this document controls.

This document discusses, among other things, systems, devices, and methods that will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
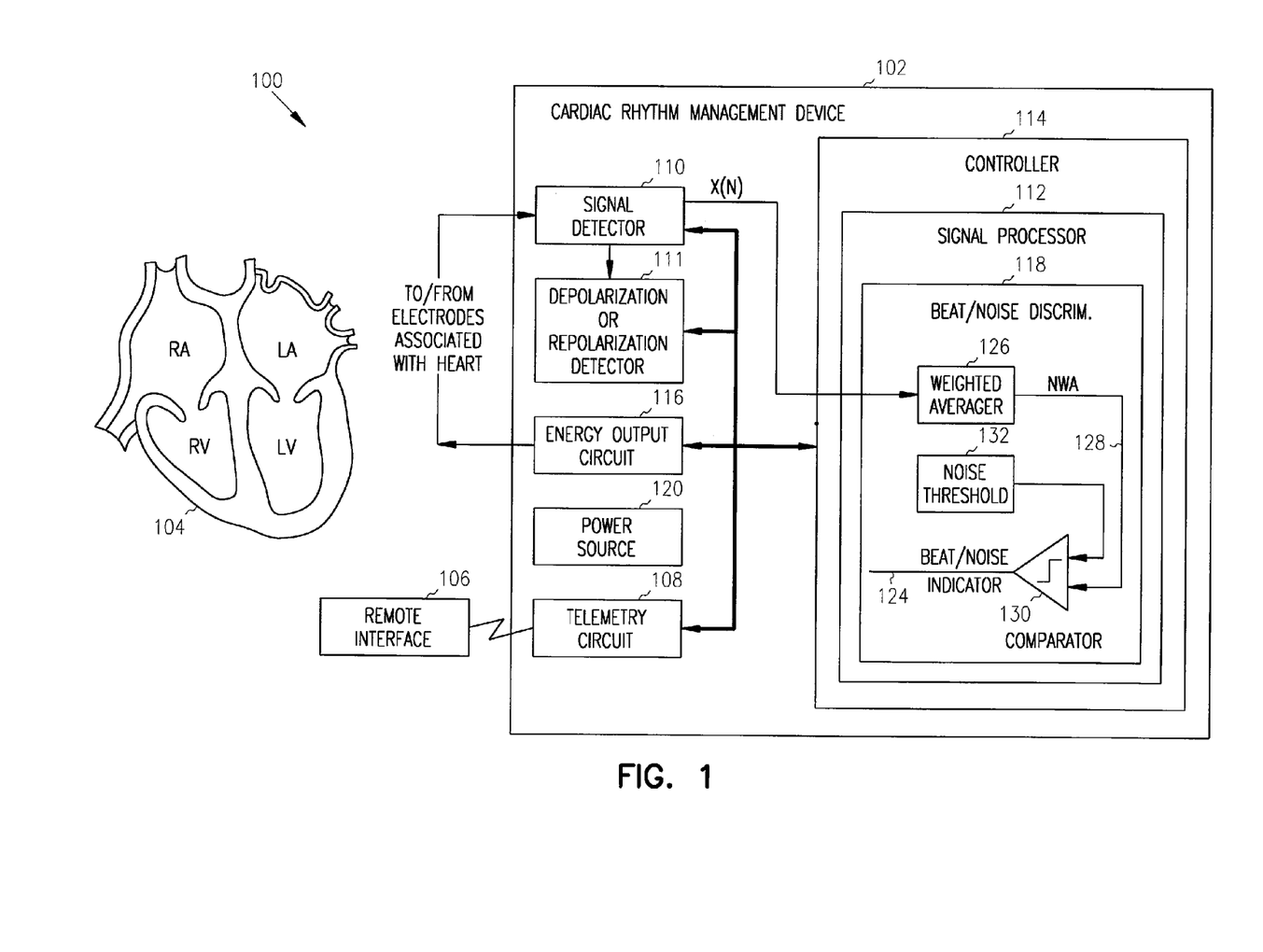
FIG. 1 is a schematic diagram illustrating generally, by way of example, but not by way of limitation, portions of a cardiac rhythm management system.

FIG. 1 is a block diagram illustrating generally portions of a cardiac rhythm management system 100 and portions of an environment in which it is used. In this example, system 100 includes a cardiac rhythm management device 102 coupled to a heart 104 by one or more electrodes associated with heart 104, such as for sensing intrinsic cardiac signals and/or for delivering energy or other therapy to heart 104. System 100 also includes a programmer or other remote interface 106, which is wirelessly or otherwise communicatively coupled to a telemetry circuit 108 or other communication circuit in device 102. Device 102 includes a pacer, a defibrillator, a cardiac resynchronization therapy (CRT) device, a monitor, a device that combines more than one of these functions, or any other implantable or external device for diagnosing and/or treating the heart. In one example, device 102 is sized and shaped for being pectorally or abdominally implanted in a human patient. The electrode(s) coupling device 102 to heart 104 may include an intravascular electrode, an intracardiac electrode, an epicardial electrode, or a housing or a header electrode located on a housing of device 102 or a header attached thereto, or any combination of the above. In some configurations, such as where portion(s) of device 102 are external to the patient, the electrode(s) coupling device 102 to heart 104 may include a skin surface electrode external to the patient. The electrodes may be associated with the heart for bipolar (i.e., two electrodes that are relatively close together) or for unipolar (i.e., two electrodes that are farther apart) signal sensing or therapy energy delivery (e.g., pacing pulse or shocks). In one example, the electrodes include a tip electrode located at or near a right ventricular apex of heart 104 and a shock or coil electrode located slightly superior thereto within the right ventricle of heart 104.

In the example of FIG. 1, device 102 includes a cardiac signal detector 110 having an input coupled to heart 104 by electrodes associated with heart 104 in a suitable manner for sensing an intrinsic cardiac signal. Detector 110 need not actually extract heart depolarizations or repolarizations from the sensed intrinsic cardiac signal; such functions may be performed elsewhere in device 102, such as by depolarization or repolarization detector 111. Detector 110 typically includes a sense amplifier for acquiring and amplifying the cardiac signal. Detector 110 may also include one or more continuous-time and/or discrete time (e.g., switched-capacitor) filter circuits, such as for selectively emphasizing the desired heart depolarization or repolarization information relative to other acquired signal content. Detector 110 may also include an analog-to-digital converter (ADC) to convert continuous-time and/or discrete time samples into numerical representations of those samples. Detector 110 may also include one or more digital filters (or other digital signal processing circuitry) following the ADC, such as for selectively emphasizing the desired heart depolarization or repolarization information relative to other acquired signal content. Detector 110 also includes an output providing a periodically sampled data cardiac signal x(n) to a cardiac signal processor module 112 of controller 114. Controller 114 is capable of sequencing through various control states such as, for example, by using a digital microprocessor having executable instructions stored in an associated instruction memory circuit, a microsequencer, or a state machine. In operation, by executing these instructions, controller 114 provides the functionality of cardiac signal processor module 112, as well as providing control signals to cardiac signal detector 110, depolarization or repolarization detector 111, and an energy output circuit 116. In one example, cardiac signal processor module 112 includes a beat/noise discrimination module 118, which is further discussed below. Energy output circuit 116 provides pacing or resynchronization pulses, antitachyarrhythmia pacing (ATP) pulses, defibrillation shocks, lower energy cardioversion shocks, and/or other appropriate cardiac therapy to heart 104. Device 102 also includes a battery or other power source 120.

In the example of FIG. 1, device 102 includes a cardiac signal detector 110 having an input coupled to heart 104 by electrodes associated with heart 104 in a suitable manner for sensing an intrinsic cardiac signal. Detector 110 need not actually extract heart depolarizations or repolarizations from the sensed intrinsic cardiac signal; such functions may be performed elsewhere in device 102, such as by depolarization or repolarization detector 111. Detector 110 typically includes a sense amplifier for acquiring and amplifying the cardiac signal. Detector 110 may also include one or more continuous-time and/or discrete time (e.g., switched-capacitor) filter circuits, such as for selectively emphasizing the desired heart depolarization or repolarization information relative to other acquired signal content. Detector 110 may also include an analog-to-digital converter (ADC) to convert continuous-time and/or discrete time samples into numerical representations of those samples. Detector 110 may also include one or more digital filters (or other digital signal processing circuitry) following the ADC, such as for selectively emphasizing the desired heart depolarization or repolarization information relative to other acquired signal content. Detector 110 also includes an output providing a periodically sampled data cardiac signal x(n) to a cardiac signal processor module 112 of controller 114. Controller 114 is capable of sequencing through various control states such as, for example, by using a digital microprocessor having executable instructions stored in an associated instruction memory circuit, a microsequencer, or a state machine. In operation, by executing these instructions, controller 114 provides the functionality of cardiac signal processor module 112, as well as providing control signals to cardiac signal detector 110, depolarization or repolarization detector 111, and an energy output circuit 116. In one example, cardiac signal processor module 112 includes a beat/noise discrimination module 118, which is further discussed below. Energy output circuit 116 provides pacing or resynchronization pulses, antitachyarrhythmia pacing (ATP) pulses, defibrillation shocks, lower energy cardioversion shocks, and/or other appropriate cardiac therapy to heart 104. Device 102 also includes a battery or other power source 120.

Figure 2:
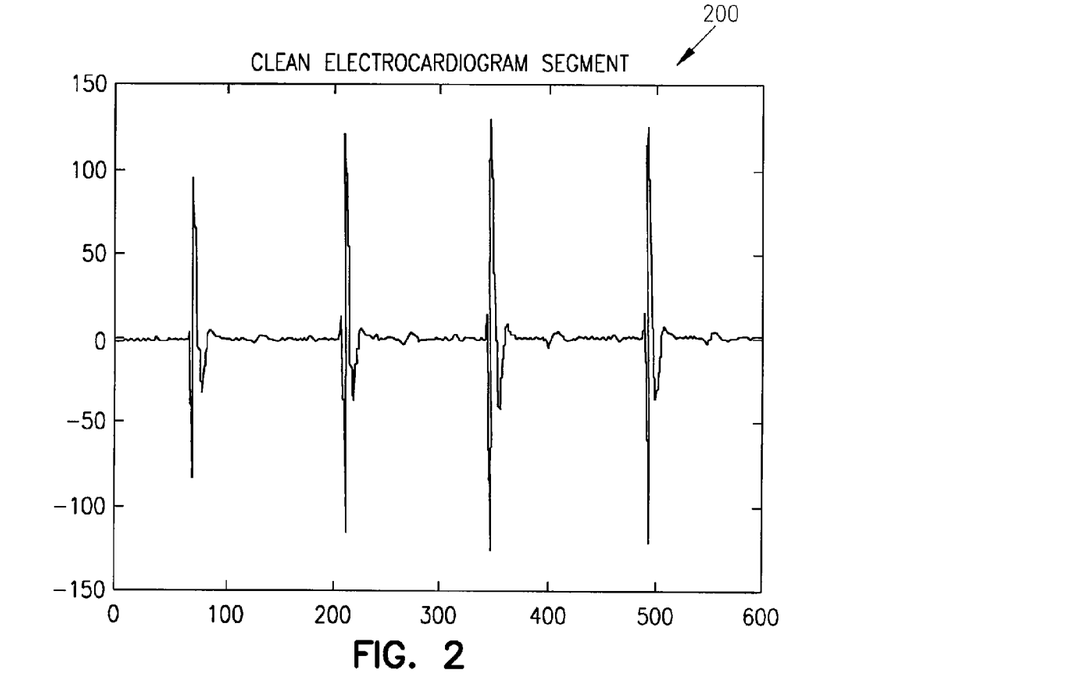
FIG. 2 is a graph illustrating generally a relatively noise-free cardiac signal.
Figure 3A:
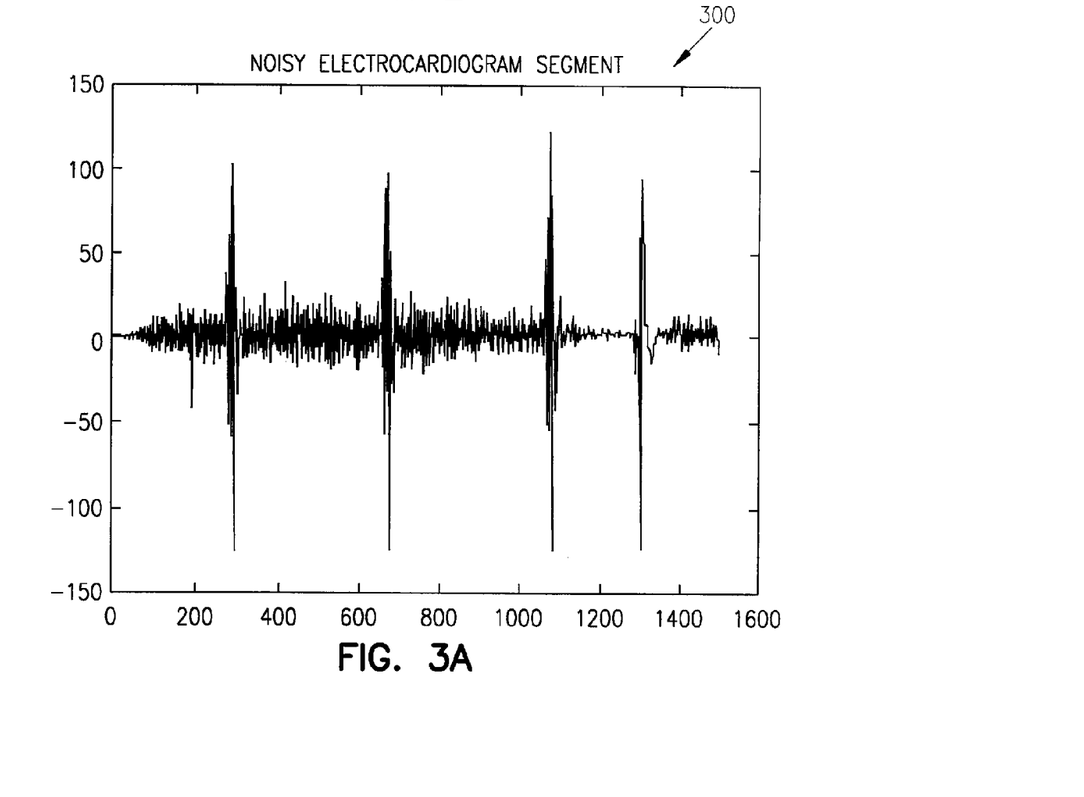
FIG. 3A is a graph illustrating generally a relatively noisy cardiac signal.

FIG. 2 is a graph illustrating generally a relatively noise-free cardiac signal 200 obtained from electrodes associated with heart 104. FIG. 3A is a graph illustrating generally a relatively noisy cardiac signal 300 similarly obtained from electrodes associated with heart 104. In the example of FIG.

Figure 3B:
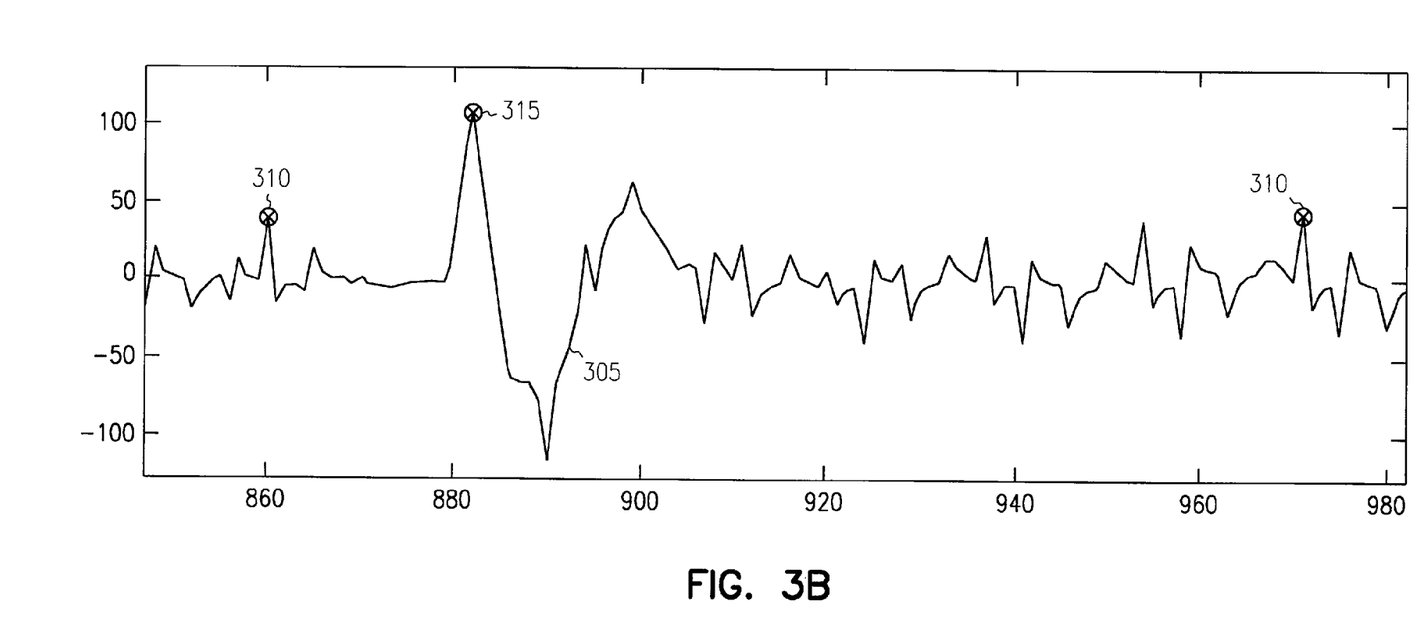
FIG. 3B is a graph illustrating in more detail a portion of a relatively noisy sampled cardiac signal.

3A, the additional noise may make the underlying heart chamber depolarizations or repolarizations difficult to detect, since the noise may include frequencies within the passband of the depolarizations or repolarizations and may, therefore, erroneously be level-detected as an actual heart depolarization or repolarization. FIG. 3B is a graph illustrating in more detail a portion of a relatively noisy sampled cardiac signal 305, which is similarly obtained from electrodes associated with heart 104. The example of FIG. 3B illustrates, among other things, noise peak amplitude samples 310 and a cardiac beat peak amplitude sample 315. As illustrated by the example of FIG. 3B, the morphology and slew rate about noise peak sample 310 is different from that about cardiac beat peak sample 315. As described below, such differences can be used to distinguish between a noise peak sample and a cardiac depolarization or repolarization peak sample. This information, in turn, may be used to avoid the inappropriate withholding or delivery of therapy based on an erroneous detection of a noise peak sample as a cardiac beat.

In the example of FIG. 1, a cardiac or other signal processor 112 includes a beat/noise discrimination module 118. Beat/noise discrimination module 118 includes an input, at node/bus 122, that receives the sampled cardiac or other signal x(n), Beat/noise discrimination module 118 also includes an output, at node/bus 124, providing a beat/noise indicator that provides a determination of whether an amplitude peak on the sampled signal x(n) represents a heart beat or is instead merely indicative of noise. In one example, the beat/noise discrimination determination is made using a central tendency computing circuit such as a weighted averager 126, which receives the sampled signal x(n) and computes a central tendency such as a weighted average that is output at node/bus 128. In one example, the weighted average is a normalized weighted average (NWA). In one example, a normalized weighted average is computed according to Equation 1.

$$NWA=[P(n-1)+2*P(n)+P(n+1)]/[4*P(n)] \quad (1)$$

In Equation 1, P(n) represents a peak amplitude sample of the sampled signal x(n), P(n−1) represents the sample immediately preceding the peak amplitude sample P(n), and P(n+1) represents the sample immediately subsequent to the peak amplitude sample P(n). In one example, the peak amplitude sample P(n) is that peak amplitude sample corresponding to a peak amplitude of a depolarization or repolarization detected by depolarization or repolarization detector 111. In one example, in which the sampled signal x(n) is sampled at a 200 Hz sample rate, a 5 millisecond time interval separates the samples P(n) and P(n−1) and the samples P(n) and P(n+1). In another example, in which the sampled signal x(n) is sampled at a 256 Hz sample rate, about a 3.9 millisecond time interval separates the samples P(n) and P(n−1) and the samples P(n) and P(n+1). These examples are merely illustrative; other sample rates are also possible. Moreover, Equation 1 need not be limited to using the immediately preceding and subsequent samples, but could alternatively use other preceding and subsequent samples, such as illustrated by way of example, but not by way of limitation, in Equation 2.

$$NWA=[P(n-k)+2*P(n)+P(n+k)]/[4*P(n)] \quad (2)$$

In Equation 2, $k \geq 2$ can be used, such as, for example, at higher sampling rates (for example, sampling rates greater than or equal to 512 kHz). In one example, the samples preceding and subsequent to peak sample, P(n), are selected to fall within the time period of the corresponding depolarization or repolarization to be distinguished from noise. For example, a QRS depolarization complex of a ventricular contraction typically exhibits a corresponding cardiac signal deviation away from baseline that lasts between 80 milliseconds and 120 milliseconds. For P(n), P(n−1), and P(n+1) to fall within a 120 millisecond QRS depolarization, the time difference between the peak sample and the preceding sample should be less than about 60 milliseconds; similarly, the time difference between the peak sample and the subsequent sample should be less than about 60 milliseconds. For P(n), P(n−1), and P(n+1) to fall within an 80 millisecond QRS depolarization, the time difference between the peak sample and the preceding sample should be less than about 40 milliseconds; similarly, the time difference between the peak sample and the subsequent sample should be less than about 40 milliseconds. These examples are offered for illustrative purposes, and are not intended to be limiting.

In the above example, as illustrated by Equations 1 and 2, the weighted averages are normalized. For example, in one embodiment, cardiac or other signal detector 110 includes an automatic gain control (AGC) circuit, which adjusts the amplitude of the detected depolarizations or repolarizations to make better use of the available dynamic range of the signal processing circuits. In such an example, normalization of the weighted average to the peak value of the depolarization or repolarization may be desirable to eliminate the effect of the AGC in computing the weighted average. In another example, in which cardiac signal detector 110 does not include such an AGC, no normalization to the peak value of the depolarization or repolarization need be used. In a non-normalized example, the term P(n) is removed from the denominator of Equations 1 and 2 to compute a non-normalized weighted average.

Figure 4:
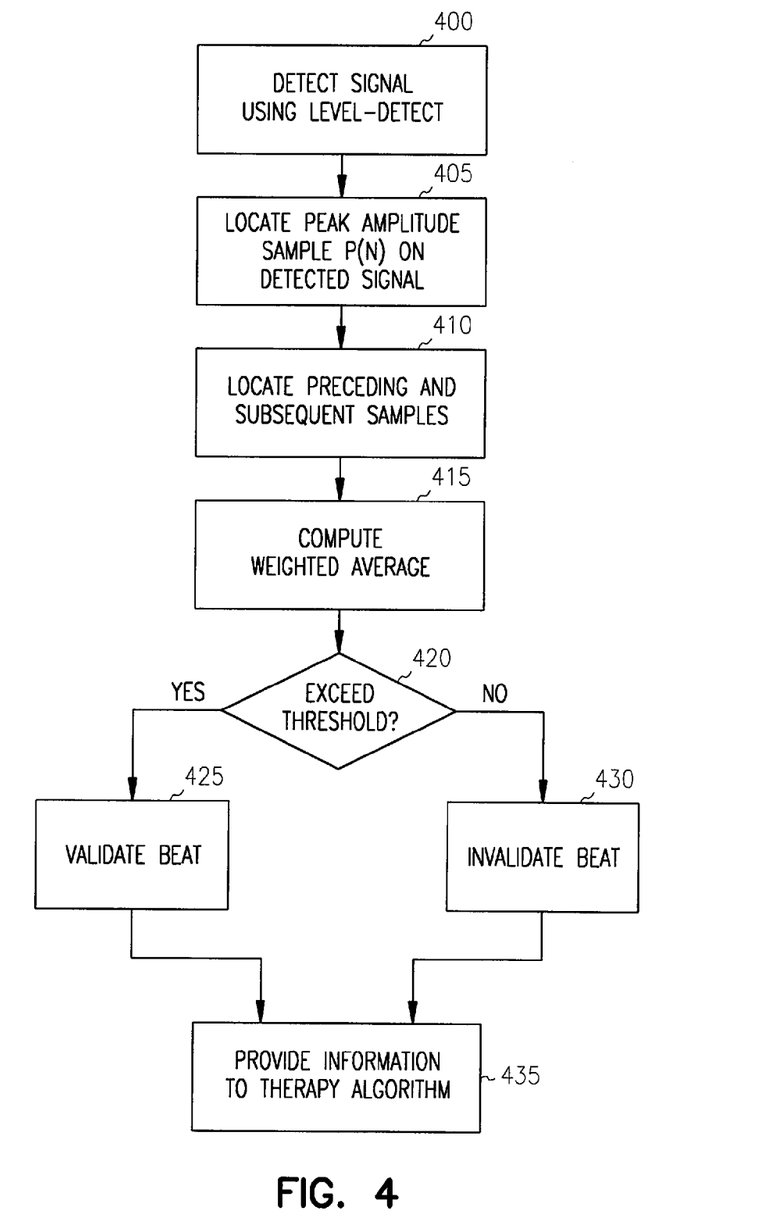
FIG. 4 is a flow chart illustrating generally, by way of example, but not by way of limitation, using a weighted average to validate or invalidate a depolarization or repolarization detected by level-detecting or one or more other techniques.
Figure 5:
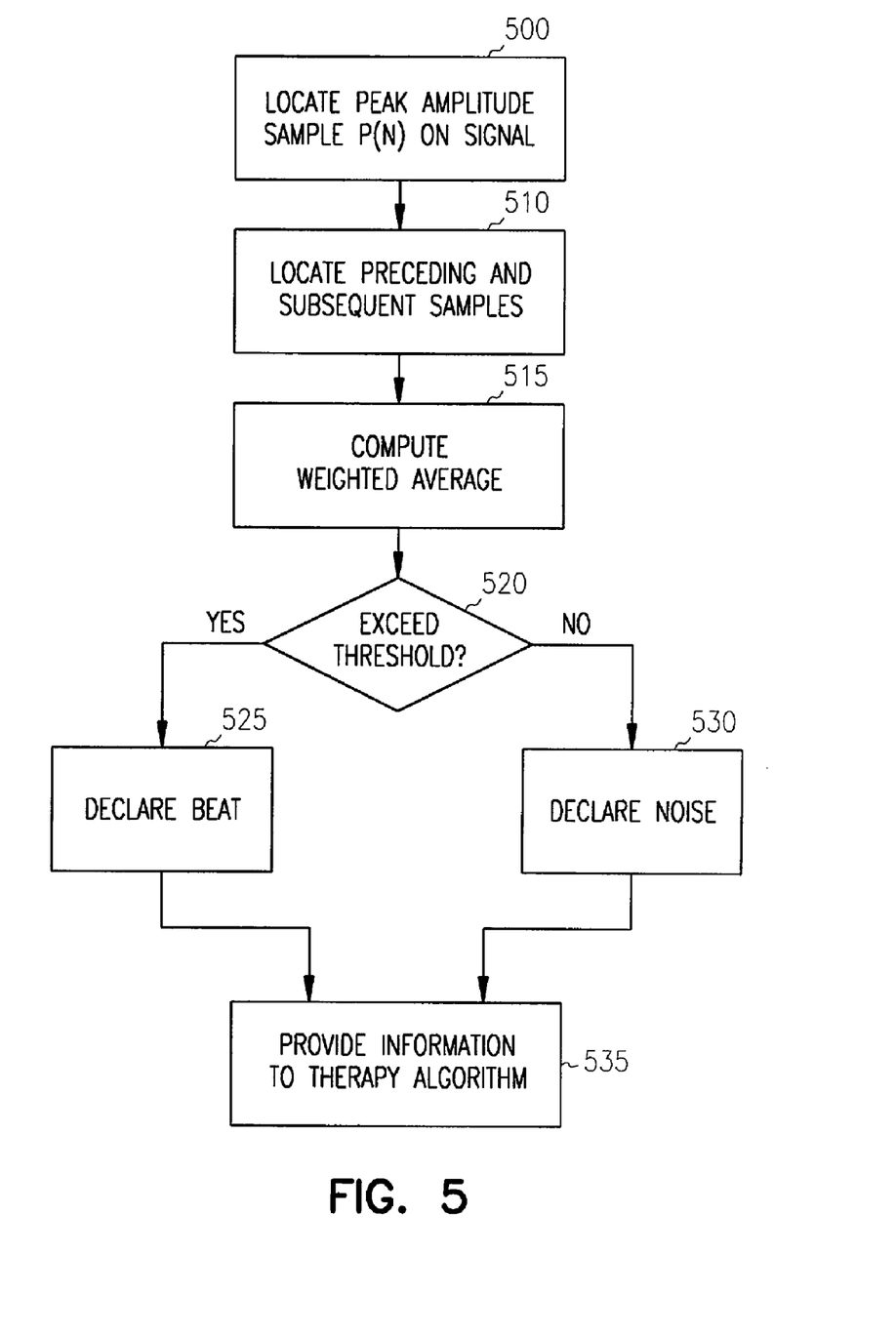
FIG. 5 is a flow chart illustrating generally, by way of example, but not by way of limitation, using a weighted average to detect a depolarization or repolarization.

In the example of FIG. 1, beat/noise discrimination module also includes a hardware, software, or firmware comparator 130 that compares the computed NWA to a specified noise threshold 132. If the computed NWA exceeds the noise threshold 132, then the peak sample is deemed a beat; otherwise it is deemed to be noise. An indication of whether the peak sample is a beat or noise is output at node/bus 124. In one example, controller 114 provides one or more cardiac rhythm management therapy control signals that trigger therapy delivery by energy output circuit 116. Controller 114 includes one or more algorithms that determine whether therapy is needed using heart rhythm information that is based on detected depolarizations or repolarizations. The level-detecting or other techniques used by depolarization or repolarization detector 111 to detect a heart depolarization or repolarization may be susceptible to myopotential or other noise that may inappropriately inhibit, or inappropriately trigger, therapy delivery. Beat/noise discrimination module 118 provides at least one additional criteria to validate (or invalidate, i.e., deem as noise) a depolarization or repolarization detected by depolarization or repolarization detector 111. Alternatively, beat/noise discrimination module 118 may replace depolarization or repolarization detector 111 to detect a depolarization or repolarization rather than validating or invalidating an already-detected depolarization or repolarization. FIGS. 4 and 5 illustrate examples of these different operating modes.

FIG. 4 is a flow chart illustrating generally, by way of example, but not by way of limitation, using a weighted average to validate or invalidate a depolarization or repolarization detected by level-detecting or other techniques. In the example of FIG. 4, at 400, a depolarization or repolarization is detected, such as by depolarization or repolarization detector 111 using level detecting and/or other techniques. At 405, a peak amplitude sample P(n) is located at the peak amplitude of the detected depolarization or repolarization. At 410, an immediately preceding sample P(n−1) and an immediately subsequent sample P(n+1) are located. At 415, a weighted average is computed, such as described in the examples of Equations 1 or 2. At 420, if the weighted average exceeds a specified threshold, the depolarization or repolarization detected at 400 is validated at 425 as an actual beat; otherwise the depolarization or repolarization detected at 400 is invalidated at 430, i.e., deemed noise. At 435, an indication of whether the depolarization or repolarization detected at 400 was validated or invalidated is provided to a therapy algorithm used by controller 114, such as for determining whether the heart rhythm indicates that responsive therapy should be delivered by device 102.

FIG. 5 is a flow chart illustrating generally, by way of example, but not by way of limitation, using a weighted average to detect a depolarization or repolarization. In the example of FIG. 5, at 500, a peak amplitude sample P(n) is located on the sampled cardiac signal x(n), such as by using a digital peak detector. At 510, an immediately preceding sample P(n−1) and an immediately subsequent sample P(n+1) are located. At 515, a weighted average is computed, such as described in the example of Equations 1 or 2. At 520, if the weighted average exceeds a specified threshold, a detected depolarization or repolarization is declared at 525; otherwise the peak amplitude sample is declared noise at 530. At 535, an indication of whether a depolarization was detected and declared at 525 is provided to a therapy algorithm used by controller 114, such as for determining whether the heart rhythm indicates that responsive therapy should be delivered by device 102.

Figure 6:
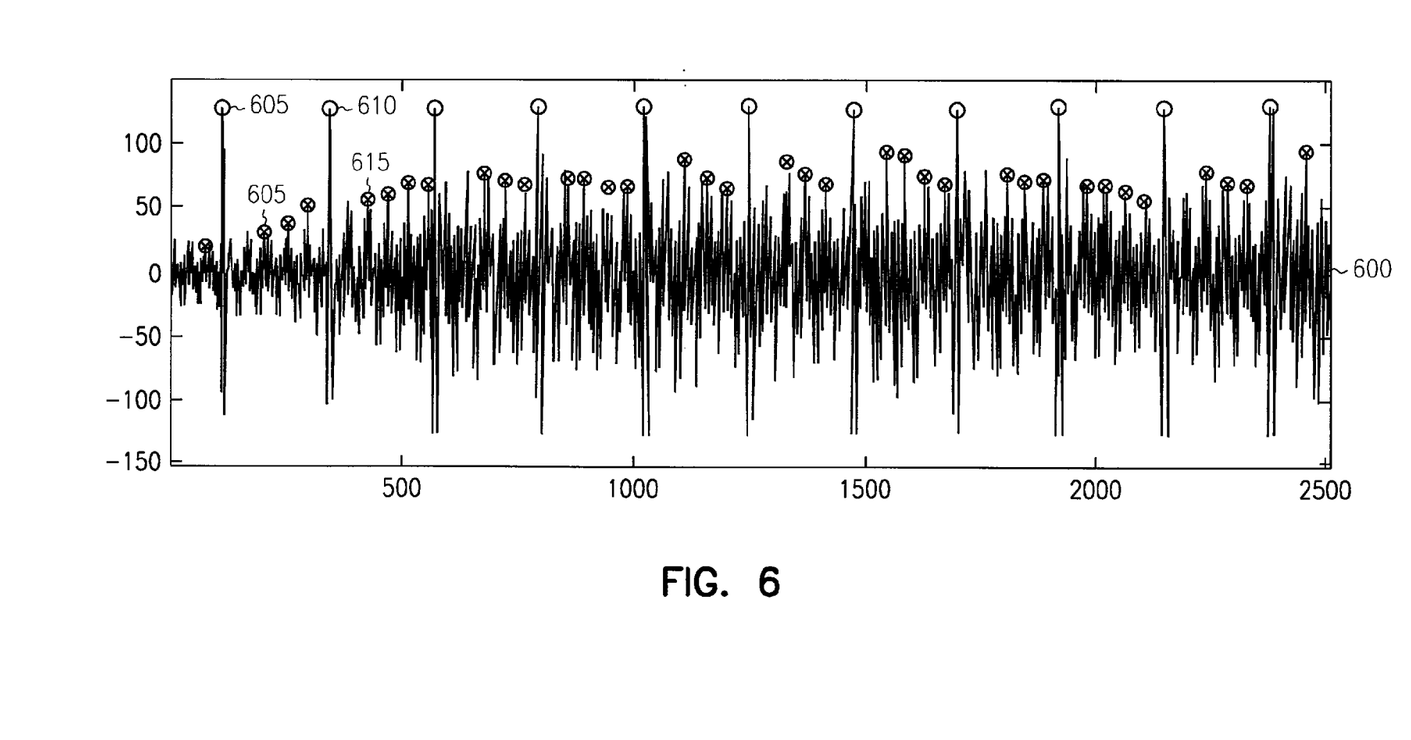
FIG. 6 is a graph illustrating generally, by way of example, but not by way of limitation, experimental data in which detected depolarizations were validated using the technique described in the flow chart of FIG. 4.

FIG. 6 is a graph illustrating generally, by way of example, but not by way of limitation, experimental data in which detected depolarizations were validated using the technique described in the flow chart of FIG. 4. In the example of FIG. 6, heart signal 600 was obtained from (1) right ventricular apical tip and (2) right ventricular shock coil electrodes associated with a subject's heart 104. The amplitude peaks of heart signal 600 that are marked by circles (such as 605) represent level-detected depolarizations. The level-detected depolarizations marked by open circles (such as 610) were validated as actual cardiac beats. The level-detected depolarizations that are marked by circles having X's (such as 615) were invalidated as actual cardiac beats, i.e., deemed noise. In this example, a specified noise threshold 132 value of 0.62 was used. The average value of NWA for actual beats was 0.89, with a standard deviation of 0.08. The average value of NWA for noise peaks was 0.43, with a standard deviation of 0.08.

In a further example, a refractory period is used in conjunction with the validation technique illustrated in FIG. 4. In this example, any beat that is validated at 425 is followed by a refractory period of specified duration (e.g., between about 40 milliseconds and about 80 milliseconds). During the refractory period, all observed peak amplitude signals are deemed noise. Only after the refractory period expires are subsequent amplitude peaks validated or invalidated using the weighted average techniques described in this document.

Figure 7:
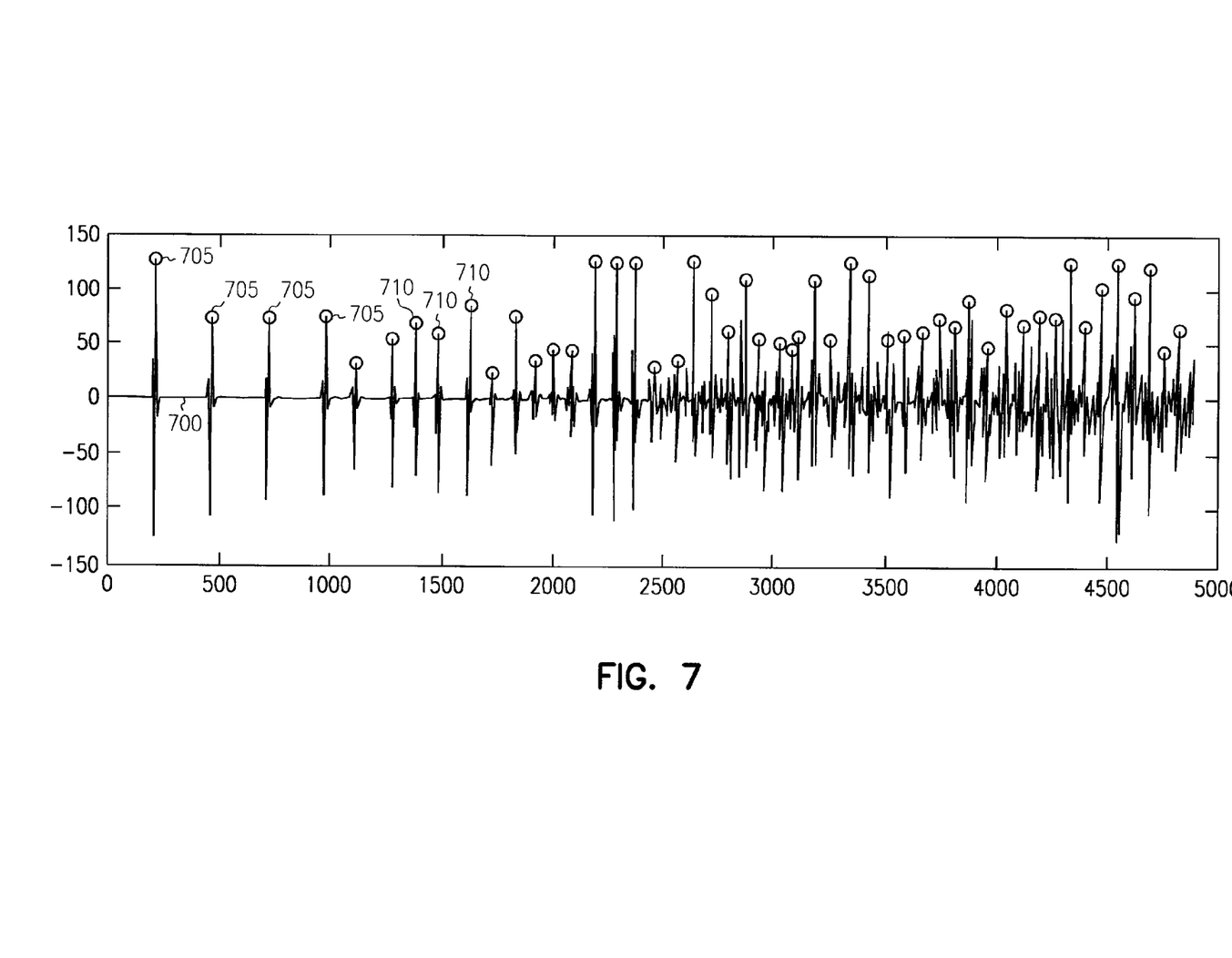
FIG. 7 is a graph illustrating generally, by way of example, but not by way of limitation, experimental data in which detected depolarizations (during the onset of ventricular fibrillation) were validated using the technique described in the flow chart of FIG. 4.

FIG. 7 is a graph illustrating generally, by way of example, but not by way of limitation, experimental data in which detected depolarizations (during the onset of an arrhythmia, such as ventricular fibrillation) were validated using the technique described in the flow chart of FIG. 4. Unlike the example of FIG. 6, for which depolarizations were validating during normal sinus rhythm (NSR), in FIG. 7, depolarizations were validated during the onset of a ventricular fibrillation (VF) episode. The morphologies (shapes) of NSR cardiac complexes may differ substantially from those of VF cardiac signals. However, as illustrated by FIG. 7, the technique described in the flow chart of FIG. 4 is also effective at distinguishing cardiac complexes from noise even when such cardiac complexes are VF signals instead of NSR complexes. In FIG. 7, the circles 705 represent level-detected cardiac depolarizations that were validated as actual cardiac beats during normal sinus rhythm. The circles 710 (e.g., the seventh and all subsequent beats illustrated in FIG. 7) represent level-detected cardiac depolarizations that were validated as actual cardiac beats during ventricular fibrillation, despite significant fluctuations in the cardiac signal due to the ventricular fibrillation. Heart signal 700 represents a period of time before and during the onset of a VF episode. Heart signal 700 was obtained from (1) right ventricular apical tip and (2) right ventricular shock coil electrodes associated with a subject's heart 104. In this example, a specified noise threshold 132 value of 0.62 was used.

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, in the following claims, the terms "first," "second," "third," etc. are used merely as labels, and are not intended to impose numeric requirements on their objects.

What is claimed is:

1. A system comprising:
    a signal detector, comprising a detector input and comprising a detector output providing a physiologic sampled signal; and
    a signal processor circuit, coupled to the detector output, the signal processor circuit configured to distinguish, using a peak sample, a preceding sample to the peak sample, and a subsequent sample to the peak sample, a signal depolarization or repolarization from noise, and in which the signal processor circuit is configured to form a weighted average computed using as data points an amplitude of the peak sample from a baseline, an amplitude of the preceding sample from the same baseline, and an amplitude of the subsequent sample from the same baseline, wherein the preceding sample and the subsequent sample are specified adjustably according to a sample rate, and to distinguish a signal depolarization or repolarization from noise by comparing the weighted average to a specified threshold value.

2. The system of claim 1, in which the signal processor circuit is configured to compute a normalized weighted average using the peak sample, the preceding sample, and the subsequent sample, and to distinguish a signal depolarization or repolarization from noise by comparing the normalized weighted average to a specified threshold value.

3. The system of claim 2, in which the normalized weighted average (NWA) is computed as NWA=[P(n−k)+2*P(n)+P(n+k)]/[4*P(n)], wherein P(n) represents the peak sample, P(n−k) represents the preceding sample, P(n+k) represents the subsequent sample, and k is a positive integer determined according to the sample rate.

4. The system of claim 1, further comprising an electrode coupled to the detector input.

5. The system of claim 4, further comprising an intracardiac leadwire carrying the electrode.

6. The system of claim 1, further comprising:
    an implantable device including the signal detector and the signal processing circuit; and a remote user interface, configured to be communicatively coupled to the implantable device.

7. The system of claim 1, in which the signal processor circuit is configured to distinguish a normal sinus rhythm depolarization or repolarization from noise.

8. The system of claim 1, in which the signal processor circuit is configured to distinguish an arrhythmic depolarization or repolarization from noise.

9. The system of claim 8, in which the signal processor circuit is configured to distinguish a ventricular fibrillation depolarization or repolarization from noise.

10. The system of claim 1, wherein the signal processing circuit is configured to exclude a peak sample detected during a refractory period from the forming of the weighted average.

11. An implantable cardiac rhythm management device comprising:
a signal detector, comprising a signal detector input and comprising a signal detector output providing a physiologic sampled signal; and
a depolarization or repolarization detector circuit, coupled to the first electrode, the depolarization or repolarization detector circuit including a level detector circuit configured to detect an intrinsic depolarization or repolarization on the intrinsic signal; and
a signal processor circuit, coupled to the signal detector output and the depolarization or repolarization detector circuit, the signal processor circuit configured to validate the intrinsic depolarization or repolarization detected by the depolarization or repolarization detector circuit by distinguishing a depolarization or repolarization from noise, using a weighted average computed using as data points an amplitude, from a baseline, of a peak sample of the sampled signal, an amplitude, from the same baseline, of a preceding sample to the peak sample of the sampled signal, and an amplitude, from the same baseline, of a subsequent sample to the peak sample of the sampled signal, wherein the peak sample of the sampled signal is associated with a peak of the intrinsic depolarization or repolarization detected by the depolarization or repolarization detector circuit, and wherein the preceding sample and the subsequent sample are specified adjustably according to a sample rate.

12. The system of claim 11, in which the weighted average (NWA) is computed as NWA=[P(n−k)+2*P(n)+P(n+k)]/[4*P(n)], wherein P(n) represents the peak sample, P(n−k) represents the preceding sample, P(n+k) represents the subsequent sample, and k is a positive integer determined according to the sample rate.

13. The system of claim 11, in which the signal processor circuit is configured to distinguish a normal sinus rhythm depolarization or repolarization from noise.

14. The system of claim 11, in which the signal processor circuit is configured to distinguish an arrhythmic depolarization or repolarization from noise.

15. The system of claim 11, in which the signal processor circuit is configured to distinguish a ventricular fibrillation from noise.

16. A method comprising:
sampling a physiological signal;
detecting a peak sample from the signal;
detecting a preceding sample to the peak sample from the signal;
detecting a subsequent sample to the peak sample from the signal;
distinguishing, using the peak sample, the preceding sample, and the subsequent sample, a depolarization or repolarization from noise, in which the distinguishing comprises:
computing a weighted average, the statistic computed using as data points an amplitude of the peak sample from a baseline, an amplitude of the preceding sample from the same baseline, and an amplitude of the subsequent sample from the same baseline, wherein the preceding sample and the subsequent sample are specified adjustably according to a sample rate; and
distinguishing a depolarization or repolarization from noise by comparing the weighted average to a specified threshold value.

17. The method of claim 16, in which the computing comprises:
computing a normalized weighted average using the peak sample, the preceding sample, and the subsequent sample; and
distinguishing a cardiac depolarization or repolarization from noise by comparing the normalized weighted average to a specified threshold value.

18. The method of claim 16, in which the computing the normalized weighted average (NWA) is computed as NWA= [P(n−k)+2*P(n)+P(n+k)]/[4*P(n)], wherein P(n) represents the peak sample, P(n−k) represents the preceding sample, P(n+k) represents the subsequent sample, and k is a positive integer determined according to the sample rate.

19. The method of claim 16, further comprising communicating an indication of whether a peak sample is a depolarization or repolarization or noise to a remote location.

20. The method of claim 16, in which the distinguishing a depolarization or repolarization from noise comprises distinguishing a normal sinus rhythm depolarization or repolarization from noise.

21. The method of claim 16, in which the distinguishing a depolarization or repolarization from noise comprises distinguishing an arrhythmic depolarization or repolarization from noise.

22. The method of claim 16, in which the distinguishing a depolarization or repolarization from noise comprises distinguishing a ventricular fibrillation depolarization or repolarization from noise.

23. A method comprising:
detecting an intrinsic physiologic signal;
detecting a depolarization or repolarization on the intrinsic signal by comparing a level of the intrinsic signal to a level threshold value to yield a level-detected depolarization or repolarization;
sampling the intrinsic signal to produce a sampled signal;
detecting a peak sample from the sampled signal, wherein the peak sample is associated with the level-detected depolarization or repolarization;
detecting a preceding sample to the peak sample from the sampled signal;
detecting a subsequent sample to the peak sample from the sampled signal; and
validating, using the peak sample, the preceding sample, and the subsequent sample, the level-detected depolarization or repolarization by computing a weighted average using the peak sample, the preceding sample, and the subsequent sample, and comparing the weighted average to a noise threshold, wherein the preceding sample and the subsequent sample are specified adjustably according to a sample rate.

24. The method of claim 23, in which the computing the weighted average (NWA) is computed as NWA=[P(n−k)+

2*P(n)+P(n+k)]/[4*P(n)], wherein P(n) represents the peak sample, P(n−k) represents the preceding sample, P(n+k) represents the subsequent sample, and k is a positive integer determined according to the sample rate.

25. The method of claim 23, in which the validating comprises validating a normal sinus rhythm depolarization or repolarization.

26. The method of claim 23, in which the validating comprises validating an arrhythmic depolarization or repolarization from noise.

27. The method of claim 23, in which the validating comprises validating a ventricular fibrillation from noise.

28. A system comprising:
a physiologic signal detector, comprising a detector input and comprising a detector output providing a physiologic sampled signal; and
a signal processor circuit, coupled to the detector output, the signal processor circuit configured to distinguish a depolarization or repolarization from noise, the distinguishing using an amplitude of a peak sample from a baseline, an amplitude, from the same baseline, of a preceding sample to the peak sample, and an amplitude, from the same baseline, of a subsequent sample to the peak sample, and in which the signal processor circuit is configured to form a weighted average of each of the amplitudes of the peak sample, the preceding sample, and the subsequent sample, and to distinguish a depolarization or repolarization from noise by comparing the weighted average to a specified threshold value, wherein the preceding sample and the subsequent sample are specified adjustably according to a sample rate.

* * * * *

UNITED STATES PATENT AND TRADEMARK OFFICE
CERTIFICATE OF CORRECTION

| | |
|---|---|
| PATENT NO. | : 8,078,272 B2 |
| APPLICATION NO. | : 11/625432 |
| DATED | : December 13, 2011 |
| INVENTOR(S) | : Lin |

It is certified that error appears in the above-identified patent and that said Letters Patent is hereby corrected as shown below:

In column 14, line 23, in Claim 18, delete "claim 16," and insert -- claim 17, --, therefor.

Signed and Sealed this
Twenty-seventh Day of March, 2012

David J. Kappos
*Director of the United States Patent and Trademark Office*